United States Patent
Gall et al.

[11] 3,947,466
[45] Mar. 30, 1976

[54] INTERMEDIATES AND PROCESS FOR THE PRODUCTION OF CERTAIN TRIAZOLOBENZODIAZEPINES

[75] Inventors: Martin Gall, Kalamazoo; Jackson B. Hester, Jr., Galesburg, both of Mich.

[73] Assignee: The Upjohn Company, Kalamazoo, Mich.

[22] Filed: June 19, 1974

[21] Appl. No.: 480,980

Related U.S. Application Data

[63] Continuation-in-part of Ser. No. 332,293, Feb. 14, 1973, Pat. No. 3,842,090.

[52] U.S. Cl. ............................ 260/308 R; 424/269
[51] Int. Cl.[2] ............................... C07D 249/08
[58] Field of Search ............................ 260/308 R

[56] References Cited
OTHER PUBLICATIONS
Allgeier et al., Chem. Abstracts, 77:126711r (1972).
Okamoto et al., Chem. Abstracts, 77:126709w (1972).

Primary Examiner—Joseph A. Narcavage
Attorney, Agent, or Firm—Hans L. Berneis

[57] ABSTRACT

A multi-step process for the preparation of 1-[(amino - or substituted amino)methyl]-6-phenyl-4H-s-triazolo-[4,3-a][1,4]benzodiazepines of the formula VI:

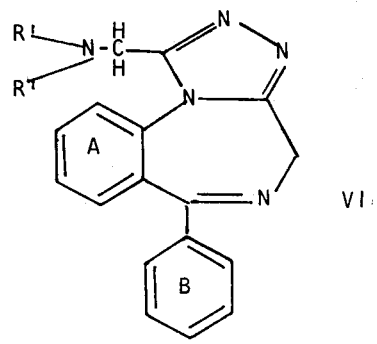

wherein R' is hydrogen or alkyl of 1 to 3 carbon atoms, inclusive, and wherein the rings A and B are unsubstituted or substituted by one or two substituents selected from the group consisting of chloro, fluoro, bromo, nitro, and trifluoromethyl, which comprises: treating a compound of the formula I:

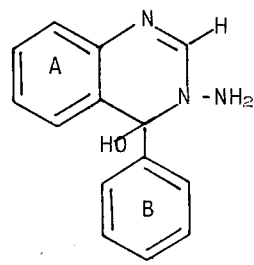

wherein rings A and B are defined as above, with acetic anhydride and formic acid to obtain compound II:

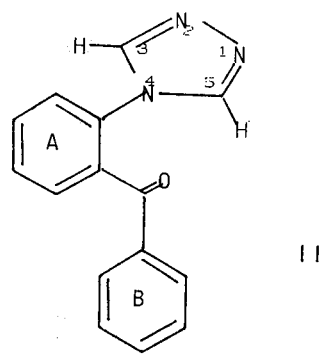

wherein A and B rings have the significance as above, treating compound II with sufficient formaldehyde to produce compound III, the 3,5-bis(hydroxymethyl)-derivative of II; treating III with phthalimide, triphenylphosphine and diethyl azodicarboxylate to give compound IV, the 3,5-bis(phthalimidomethyl) derivative of II; and treating IV with hydrazine hydrate to obtain a compound of formula V

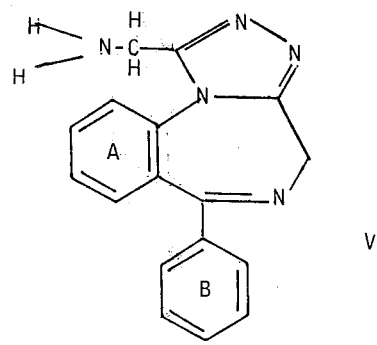

wherein rings A and B are defined, as herein above. Compound V can then be alkylated in known manner to give those compounds of formula VIa which corresponds to formula VI when R' is desired to be alkyl.

The compounds of formula VI have antidepressant and antianxiety effects in mammals and birds.

17 Claims, No Drawings

INTERMEDIATES AND PROCESS FOR THE PRODUCTION OF CERTAIN TRIAZOLOBENZODIAZEPINES

CROSS REFERENCES TO RELATED APPLICATIONS

This application is a continuation in part of application Ser. No. 332,293, filed Feb. 14, 1973 now U.S. Pat. No. 3,842,090.

BACKGROUND OF THE INVENTION

FIELD OF THE INVENTION

This invention is directed to a new process for organic compounds and is particularly concerned with a process for the production of 1-[(amino or substituted amino)methyl]-6-phenyl-4H-s-triazolo[4,3-a][1,4]benzodiazepines as well as with the new intermediates III and IV in this process.

The process of production and the novel intermediates can be illustratively represented as follows:

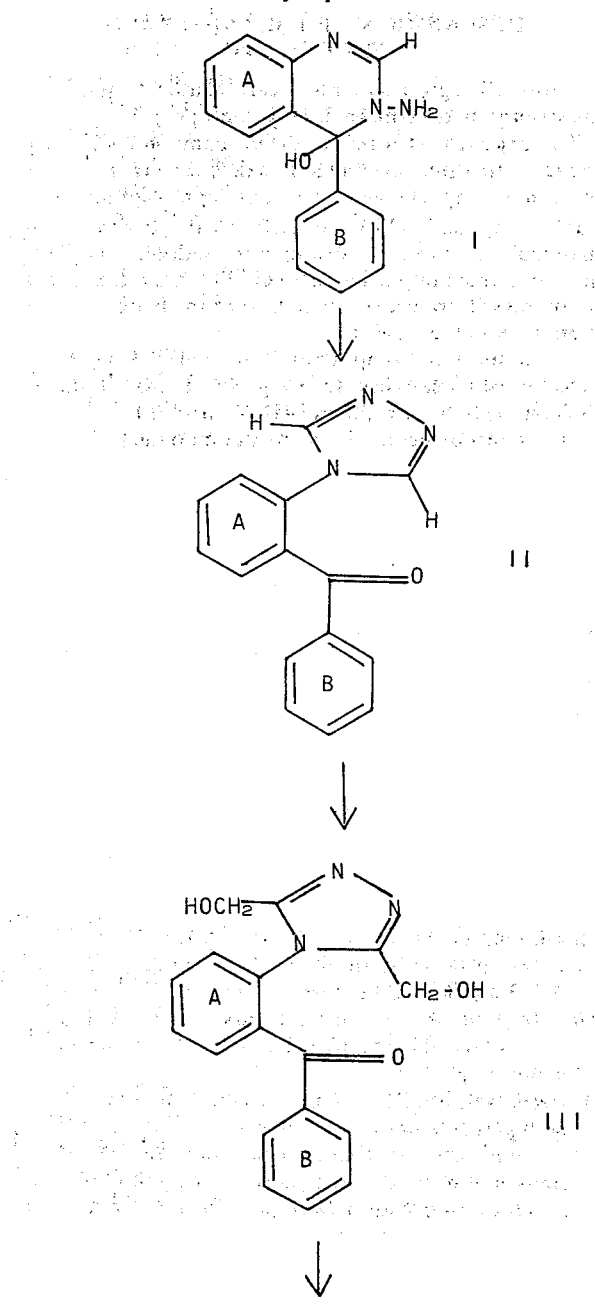

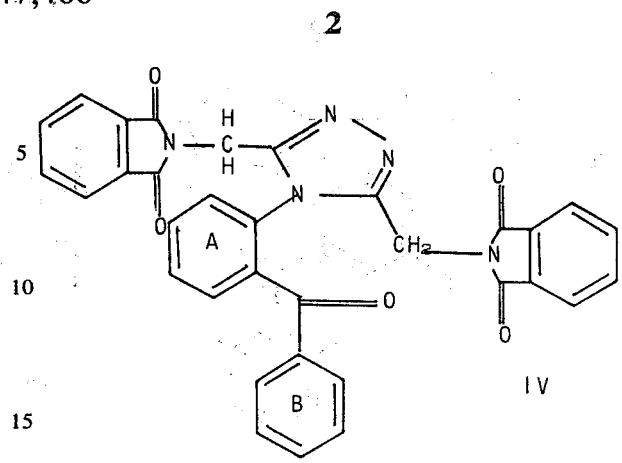

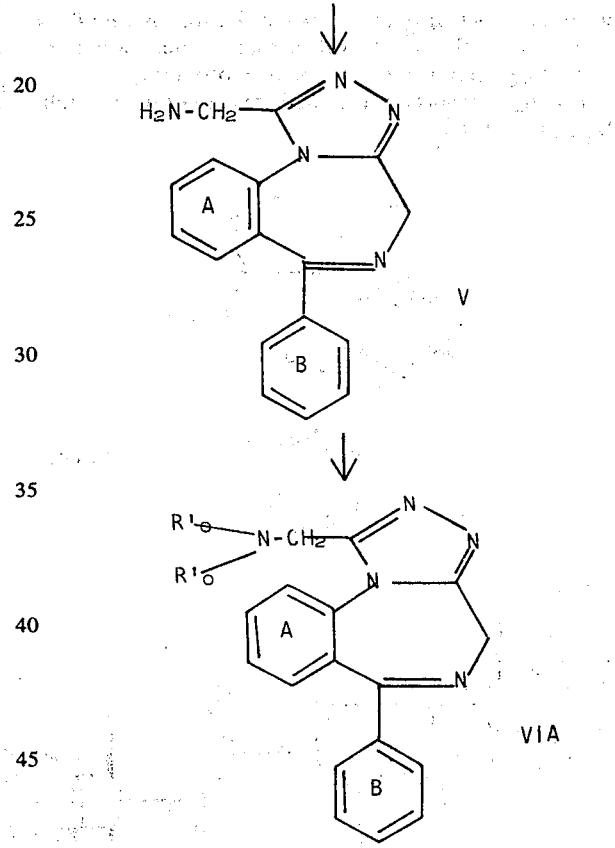

wherein R'$_o$ is alkyl; and wherein the rings A and B are unsubstituted or substituted by one or two substituents selected from the group consisting of chloro, fluoro, bromo, nitro, and trifluoromethyl.

The more important intermediates have the formulae IIIA and IVA below:

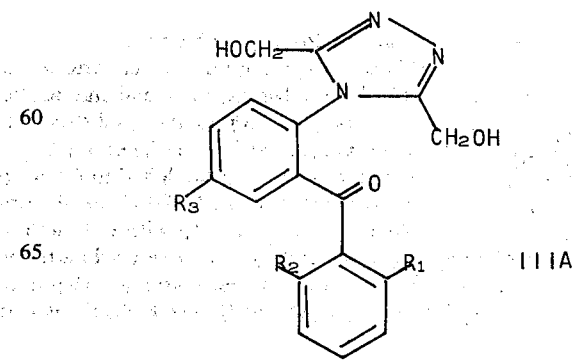

and

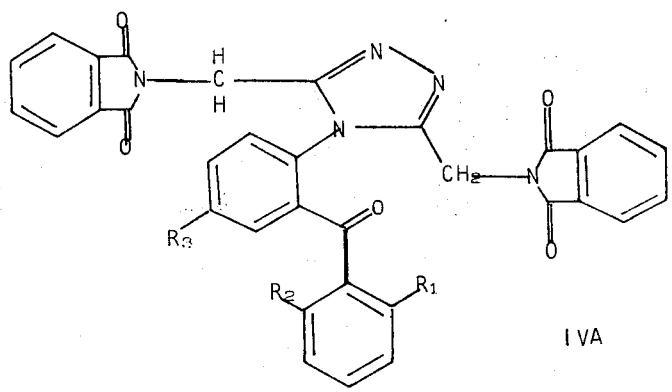

IVA wherein $R_1$ is hydrogen, chloro or fluoro; wherein $R_2$ is hydrogen, or fluoro when $R_1$ is fluoro; and wherein $R_3$ is hydrogen, chloro, fluoro, or trifluoromethyl.

The most important intermediates are of the formula IIIB and IVB below.

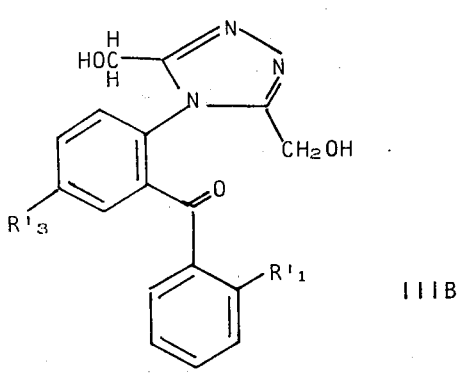

IIIB and

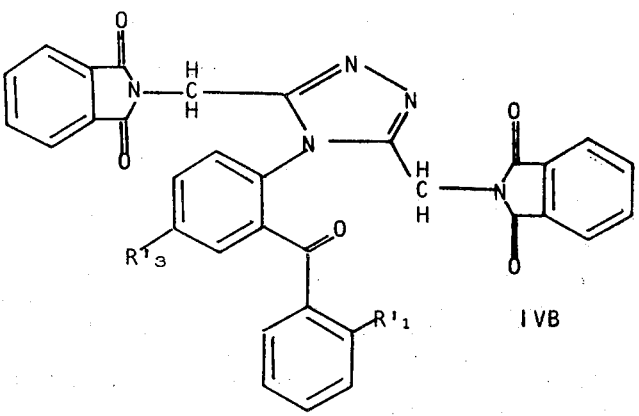

IVB wherein $R'_1$ and $R'_3$ are hydrogen or chlorine.

The process of this invention comprises: reacting a compound of formula I with formic acid and acetic anhydride at 0° to 25° to obtain compound II; and then warming the resulting mixture at 90° to 118°; heating a compound of formula II with paraformaldehyde in an inert organic solvent between 118° and 150°C. to obtain compound III; treating compound III with phthalimide, triphenylphosphine, and diethyl azodicarboxylate between 0° to 35°C, to obtain compound IV; treating IV with hydrazine hydrate at 60° – 100°C. in an alkanol of 1 to 3 carbon atoms, inclusive, to obtain compound V; and alkylating compound V with a carboxaldehyde of 1 to 3 carbon atoms inclusive, sodium cyanoborohydride and acetic acid to obtain a compound of formula VI above.

DESCRIPTION OF THE PREFERRED EMBODIMENT

Lower alkyl groups of 1 to 3 carbon atoms, inclusive, are exemplified by methyl, ethyl, and propyl.

The products of formula VI are compounds having sedative, tranquilizing and antianxiety effects. They are even more important for their antidepressant activity. Such compounds (VI) are useful in the treatment of mammals and birds; for example the sedation and antianxiety effect are particularly suitable in the treatment of animals in transit or animals kept in shelters, while their owners are absent.

The activity of compounds of formula VI has been determined by standard tests e.g.: (8-chloro-1-[(dimethylamino)methyl]-6-phenyl-4H-s-triazolo[4,3-a][1,4]benzodiazepine is the test compound)

Chimney test: [Med. Exp. 4, 145 (1961)]: The effective intraperitoneal dosage for 50% of mice ($ED_{50}$) is 2.3 mg./kg. The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of the test compound at which 50% of the mice remain in the dish. The $ED_{50}$ (intraperitoneal administration) in this test was 0.28 mg./kg.

Pedestal Test: The untreated mouse leaves the pedestal in less than a minute to climb back to the floor of the standard mouse box. Tranquilized mice will stay on the pedestal for more than 1 minute. The $ED_{50}$ (intraperitoneal administration) was 0.8 mg./kg.

Nicotine antagonism test: Mice in a group of 6 are injected with the test compound, 8-chloro-1-[(dimethylamino)methyl]-6-phenyl-4H-s-triazolo[4,3-a][1,4]benzodiazepine. Thirty minutes later the mice, including control (untreated) mice, are injected with nicotine salicylate (2 mg./kg.). The control mice show overstimulation, i.e., (1) running convulsions (2) tonic extensor fits; followed by (3) death. An intraperitoneal dosage of .11 mg./kg. of the test compound protected 50% of the animals against (3).

Antagonism to strychine (as sulfate): The effective dosage $ED_{50}$ of 8-chloro-1-[(dimethylamino)methyl]-6-phenyl-4H-s-triazolo[4,3-a][1,4]benzodiazepine is 50 mg./kg. orally in mice. The test consists in orally administering into groups of 6 mice the test compound, and 30 minutes later 3 mg./kg. strychnine sulfate intraperitoneally. The survivors after 4 hours reflect the activity of the compound as a muscle relaxant and antispasmodic. A dosage of 3 mg./kg. of strychnine sulfate is routinely fatal to all the control mice.

The following compounds have (by intraperitoneal injection) $ED_{50}$ values as shown in the table I below:

TABLE I

| COMPOUND | $ED_{50}$ (in mg./kg.) | | | |
|---|---|---|---|---|
| | Ch | D | P | Ni |
| 8-chloro-1-[(dimethylamino)methyl]-6-(o-chlorophenyl)-4H-s-triazolo[4,3-a][1,4]benzodiazepine | 0.2 | 0.36 | 0.36 | 0.63 |
| 1-[(dimethylamino)methyl]-6-(o-chlorophenyl)-4H-s-triazolo[4,3-a][1,4]benzodiazepine | 0.35 | 0.8 | 22 | 0.15 |
| 8-chloro-1-[(diethylamino)methyl]-6-(o-chlorophenyl)-4H-s-triazolo[4,3-a][1,4]-benzodiazepine | 0.63 | 0.11 | 0.4 | 0.08 |

The compounds of formula VI and pharmacologically acceptable acid addition salts and N-oxides thereof have also antidepressant activity and are thus useful for the treatment of depression in mammals or birds.

The main function of an anti-depressant is to return the depressed individual to normal functioning. This should be carefully differentiated from psychic stimulants such as the amphetamines which produce overstimulation in the normal individual.

Many different methods have been and are used to evaluate antidepressant activity. In general these methods involve antagonism to a depressant such as reserpine or tetrabenazine or a synergistic increase of the toxicity of certain compounds (i.e. yohimbine or 3,4-dihydroxyphenylalanine) and comparison of the drug action of the new compound with other known antidepressants. No single test alone can determine whether or not a new compound is an antidepressant or not, but the profile evidenced by various tests will establish the anti-depressant action if present. A number of such tests are described below.

Hypothermic tests with oxotremorine: [1-(4-pyrrolidino-2-butynyl)-2-pyrrolidinone].

Oxotremorine (as well as apomorphine and tetrabenazine) produces hypothermic responses in mice. This response is blocked by anitcholinergics and antidepressants such as atropine and imipramine respectively.

Oxotremorine produces a very pronounced hypothermia.

At a dose of 0.6 mg./kg. the body temperature of a mouse is decreased about 13° F. (when the mouse is kept at room temperature). This temperature decrease is antagonized by anti-depressants e.g. desipramine, imipramine, doxepine, and others.

The present compounds were tested as follows. Four male mice of 18-22 g. (Strain CF=Carworth Farms) were injected intraperitoneally with 1 mg. of oxotremorine. The lowering of the body temperature was measured rectally with an electronic thermometer, before and 30 minutes after drug administration. After the drug administration the mice were kept at 19° C. in cages. A 4° difference between the control mice (oxotremorine alone) and the treated mice (oxotremorine and test compound) was used to indicate the antagonistic action of the test compound.

The test results are tabulated below.

The $ED_{50}$ is the dosage of the test compound at which half the mice had a temperature of at least 4° C. higher than the control mice.

TABLE I

| COMPOUNDS | $ED_{50}$ (mg./kg.) |
|---|---|
| 8-chloro-1-[(dimethylamino)methyl]-6-phenyl-4H-s-triazolo[4,3-a][1,4]-benzodiazepine | 5.3 |
| 8-chloro-1-[(diethylamino)methyl]-6-phenyl-4H-s-triazolo[4,3-a][1,4]-benzodiazepine | 50 |
| Iprindole | >50 |
| Doxepine | 14.9 |
| Imipramine | 5.3 |

Potentiation of yohimbine aggregation toxicity: the $LD_{50}$ of yohimbine hydrochloride in mice is 45 mg./kg. i.p. Administration of 30 mg./kg. of yohimbine hydrochloride was non-lethal. If an antidepressant is administered prior to the yohimbine hydrochloride (30 mg.) the lethality of the yohimbine hydrochloride is increased.

Ten male CF mice, 18-22 g., were injected with the anti-depressant and 30 minutes later with 30 mg. of yohimbine hydrochloride (YCl) in saline solution. After two hours, the $LD_{50}$ were determined. No mice or only one mouse is killed by 30 mg. of (YCl). If (YCl) is administered in the presence of an anti-depressant an increase of the toxicity of (YCl) is observed. The $ED_{50}$ values of the new compounds and standard medicament which causes 50% of the mice to die is shown in TABLE II.

TABLE II

| [YCl] (30 mg.) control | $ED_{50}$ (mg./kg.) no death |
|---|---|
| [YCl] and 8-chloro-1-[(dimethylamino)-methyl]-6-phenyl-4H-s-triazolo[4,3-a][1,4]benzodiazepine | 12.5 |
| [YCl] and 8-chloro-1-[(diethylamino)-methyl]-6-phenyl-4H-s-triazolo[4,3-a]-[1,4]benzodiazepine | 42 |
| [YCl] and Iprindole | 20 |
| [YCl] and Imipramine | 4.4 |
| [YCl] and Doxepine | 17.7 |

Potentiation of apomorphine gnawing: a group of 4 mice (male, CF, 18–22 g.) are administered the test compound intraperitoneally one hour prior to the subcutaneous injection of apomorphine hydrochloride 10 mg./kg. The mice are then placed in a plastic box (6 × 11 × 5 inches) lined at the bottom with a cellophane-backed, absorbent paper. The degree of damage to the paper at the end of 30 minutes is scored from zero to 4. The scores 3 and 4 indicate that the compound is a potentiator of apomorphine in this test ($ED_{50}$). The results are in TABLE III.

TABLE III

| COMPOUND | $ED_{50}$ (mg./kg.) |
|---|---|
| 8-chloro-1-[(dimethylamino)methyl]-6-phenyl-4H-s-triazolo[4,3-a][1,4]-benzodiazepine | 5.3 |
| 8-chloro-1-[(diethylamino)methyl]-6-phenyl-4H-s-triazolo[4,3-a][1,4]-benzodiazepine | 14.9 |
| Iprindole | >50 |
| Imipramine | 17.7 |
| Doxepine | 17.7 |

The $LD_{50}$ values in mice for these compounds are listed in Table IV.

TABLE IV

| COMPOUND | $LD_{50}$ (mg./kg.) |
|---|---|
| 8-chloro-1-[(dimethylamino)methyl]-6-phenyl-4H-s-triazolo[4,3-a][1,4]-benzodiazepine | 476 |
| 8-chloro-1-[(diethylamino)methyl]-6-phenyl-4H-s-triazolo[4,3-a][1,4]-benzodiazepine | >100 |
| Iprindole | 450 |
| Imipramine | 178 |
| Doxepin | 126 |

The $ED_{50}$ and $LD_{50}$ values for the new compounds thus compare favorably with standard antidepressant compounds on the market.

Other compounds of formula V are anti-depressants as shown by Table V:

TABLE V

| | YO | Oxo | Ap | $LD_{50}$ |
|---|---|---|---|---|
| 8-chloro-1-(aminomethyl)-6-phenyl-4H-s-triazolo[4,3-a]-[1,4]benzodiazepine | 35.4 | 29.7 | 2.6 | >100 |
| 8-chloro-1-[(dimethylamino)-methyl]-6-(o-chlorophenyl)-4H-s-triazolo[4,3-a][1,4]benzodiazepine | >30 | >30 | 17.8 | >100 |
| 1-[(dimethylamino)methyl]-6-(o-chlorophenyl)-4H-s-triazolo-[4,3-a][1,4]benzodiazepine | >30 | >30 | >30 | >100 |

YO = Yohimbine test
Oxo = Oxotremorine test
Ap = Apomorphine test

The pharmaceutical forms contemplated by this invention include pharmaceutical compositions suited for oral, parenteral, and rectal use, e.g., tablets, powder packets, cachets, dragees, capsules, solutions, suspension, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Water or oils, e.g., coconut oil, sesame oil, safflower oil, cottonseed oil, peanut oil may be used for preparing solutions or suspensions of the active drug. Sweetening, coloring, and flavoring agents may be added.

For mammals and birds, food premixes with starch, oatmeal, dried fishmeat, fishmeal, flour, and the like can be prepared.

As tranquilizers the compounds of formula VI can be used in unit dosages of 0.02 mg. to 1 mg./kg. in oral or injectable preparations, as described above, to alleviate tension and anxiety in mammals, or birds, such as e.g., occurs when animals are in travel.

The starting compounds of this invention can be produced as shown in the preparations.

In carrying out the process of the present invention a compound of formula I is treated with an equimolar mixture of formic acid and acetic anhydride. In the preferred embodiment of this invention the compound of formula I is added to the solution of formic acid and acetic anhydride at a temperature between 0° and 25° and the mixture is kept with stirring at this temperature for 6 to 18 hours. Thereafter the reaction is completed by heating the mixture to reflux for one-half to 3 hours and the product II is recovered by conventional procedures, e.g. evaporation of the residual formic and acetic acids, dilution with water, neutralization with alkaline solution, and extraction e.g. with chloroform, methylene chloride or the like. The product II is purified by crystallization and/or chromatography.

The thus-obtained compound of formula II is heated with formaldehyde or paraformaldehyde in an inert organic solvent. When formaldehyde is used, the temperature can be 80° to 150° C or even higher if a pressure vessel is used. When paraformaldehyde is used, a temperature near the sublimation point of paraformaldehyde (120° C. at sea level) is used. Thus, in the preferred embodiment temperatures between 118° and 125° C., a nitrogen atmosphere, paraformaldehyde and a suitably high boiling inert organic solvent, e.g. xylenes (o-,m-,p- and mixtures thereof) can be used. With formaldehyde gas, toluene, heptane, Skellysolve B hexanes or C heptanes, cydoheptane, cydohexane and the like may be used. The reaction period is usually from one-half to 3 hours. After the reaction is terminated, the product III, a 2-[3,5-bis(hydroxymethyl)-4H-1,2,4-triazol-4-yl]benzophenone, is recovered by conventional methods, e.g. evaporation of the solvent in vacuo, and purification by crystallization of the product from methanol, ethanol, methylene chloride, ethyl acetate, mixtures thereof and the like.

Compound III, dissolved in an inert organic solvent, admixed with phthalimide and triphenylphosphine is reacted with diethyl azodicarboxylate at a temperature between 0° and 35° C. In the preferred embodiment of the invention phthalimide, triphenylphosphine, and diethyl azodicarboxylate are used in a ratio of 2 to 2½ mole equivalents for one mole equivalent of compound III. As solvent, dioxane, tetrahydrofuran, dipropyl ether or the like can be used. Since the reaction is slightly exothermic provisions for cooling (ice-water bath) should be made. The reaction is generally completed in 6–18 hours.

At the termination of the reaction, the reaction product IV, a 2-[3,5-bis(phthalimidomethyl)-4H-1,2,4- triazol-4-yl]benzophenone is obtained by conventional procedures such as evaporation of the solvent, extraction, chromatography and crystallization.

Compound IV is then heated with hydrazine hydrate in a lower alkanol between 60° and 100° C. As alkanols methanol, ethanol, 1- or 2-propanol are generally used with ethanol preferred. With ethanol, the time of heating is between 1 to 4 hours at about the reflux temperature. At the termination of the reaction the product V is recovered by evaporating the solvent in vacuo and the product V, a 1-(aminomethyl)-6-phenyl-4H-s-triazolo[4,3-a][1,4]benzodiazepine can be purified by extraction, chromatography or crystallization; however it can be alkylated in the next step without purification.

In general compound V is alkylated in a solvent such as tetrahydrofuran, a lower alkanol such as methanol or ethanol or preferably acetonitrile by adding a carboxaldehyde and sodium cyanoborohydride and treating the resulting mixture with an organic acid, e.g. acetic or propionic acid slowly during 30 minutes to 2 hours so that the temperature of the reaction mixture does not exceed 30°–40° C., and the pH of the mixture becomes 6.2 to 7 at the end of the reaction. The product VI, a 1-[(dialkylamino)methyl]-6-phenyl-4H-s-triazolo[4,3-a][1,4]benzodiazepine is recovered by conventional procedures, such as concentration of the reaction mixture, extraction, washing the extracts, chromatography, crystallization and the like.

The following preparations and examples are illustrative of the process and products of the present invention but are not to be construed as limiting.

Preparation 1:
2'-benzoyl-4'-chloroformanilide

2-Amino-5-chlorobenzophenone (50g) is reacted with formic acid (300 ml) at the reflux temperature of the mixture for 20 hours. At the end of the reaction the mixture is evaporated in vacuo and the crude product is crystallized from methylene chloride-hexane to give 2'-benzoyl-4'-chloroformanilide of melting point 90° to 91° C.

Preparation 2:
3-Amino-6-chloro-3,4-dihydro-4-hydroxy-4-phenyl-quinazoline

A mixture of 0.1 mole of 2'-benzoyl-4'-chloroformanilide and 0.15 mole of hydrazine are stirred at room temperature in ethanol. Stirring is continued for 20 hours. The reaction mixture is chilled, and the precipitate filtered. The solid is washed and recrystallized from dimethylformamide to give 3-amino-6-chloro-3,4-dihydro-4-hydroxy-4-phenylquinazoline.

Example 1:
5-Chloro-2-(4H-1,2,4-triazol-4-yl)benzophenone

A stirred solution of acetic anhydride (25.3 ml) and 97% formic acid (10.6 ml) is kep at ambient temperature (25°) for 30 minutes, cooled in an ice bath and treated with 3-amino-6-chloro-3,4-dihydro-4-hydroxy-4-phenylquinazoline (12.24 g, 0.0447 mole). The solution is kept at ambient temperature for 18 hours, diluted with acetic acid (25 ml), warmed to the reflux temperature during 1 hour and refluxed for 1.5 hours. The solution is concentrated in vacuo, and the residue is mixed with cold water, made alkaline with sodium hydroxide and extracted with chloroform. The extract is washed with brine, dried over anhydrous sodium sulfate and concentrated. The residue is crystallized from ethylacetate to give 7.76 g of 5-chloro-2-(4H-1,2,4-triazol-4-yl)-benzophenone of melting point 184°–186° C., 0.971 g of melting point 182.5°–184°C., and 0.144 of melting point 181°–182°C.

Crystallization of the mother liquor from the above crystallizations yields additional product which is contaminated by an impurity, insoluble in methylene chloride. Extraction of this solid with methylene chloride dissolves the product which was then crystallized from ethylacetate to give 0.565 g of additional 5-chloro-2-(4H-1,2,4-triazol-4-yl)benzophenone of melting point 183.5°–184°C.

In the same manner given in Preparations 1 and 2 and Example 1, other substituted 2-amino-benzophenones may be used to produce the corresponding 2-(4H-1,2,4-triazol-4-yl)benzophenones. Thus, in the manner given in Preparation 1, the following other benzophenones can be utilized:

4-chloro-2-aminobenzophenone;
2',5-dichloro-2-aminobenzophenone;
2',6'-difluoro-5-chloro-2-aminobenzophenone;
5-nitro-2-aminobenzophenone;
2'-chloro-5-nitro-2-aminobenzophenone;
5-trifluororomethyl-2-aminobenzophenone;
3-trifluororomethyl-2-aminobenzophenone;
2'-chloro-5-trifluoromethyl-2-aminobenzophenone;
3'-chloro-6-trifluoromethyl-2-aminobenzophenone;
2'-chloro-6-trifluoromethyl-2-aminobenzophenone;
4'-fluoro-5-trifluoromethyl-2-aminobenzophenone;
5-chloro-2'-fluoro-2-aminobenzophenone;
5-fluoro-2'-chloro-2-aminobenzophenone;
5-fluoro-2-aminobenzophenone;
6-nitro-2-aminobenzophenone;
5-bromo-2-aminobenzophenone;
5-bromo-2'-fluoro-2-aminobenzophenone;
6-bromo-2-aminobenzophenone;
2-aminobenzophenone; and the like.

From these benzophenones are then obtained (by the methods of Preparations 1 and 2 and Example 1) 2-(4H-1,2,4-triazol-4-yl)benzophenones II such as:
2',5-dichloro-2-(4H-1,2,4-triazol-4-yl)benzophenone;
2'-chloro-2-(4H-1,2,4-triazol-4-yl)benzophenone;
2'-chloro-5-nitro-2-(4H-1,2,4-triazol-4-yl)benzophenone;
2'-fluoro-5-nitro-2-(4H-1,2,4-triazol-4-yl)benzophenone;
2',6'-difluoro-5-chloro-2-(4H-1,2,4-triazol-4-yl)benzophenone;
2'-chloro-5-(trifluoromethyl)-2-(4H-1,2,4-triazol-4-yl)benzophenone;
3,4'-dichloro-2-(4H-1,2,4-triazol-4-yl)benzophenone;
5-nitro-2-(4H-1,2,4-triazol-4-yl)benzophenone;
5-fluoro-2'-chloro-2-(4H-1,2,4-triazol-4-yl)benzophenone;
2'-fluoro-2-(4H-1,2,4-triazol-4-yl)benzophenone;
5-fluoro-2-(4H-1,2,4-triazol-4-yl)benzophenone;
3'-chloro-2-(4H-1,2,4-triazol-4-yl)benzophenone;
4-chloro-2'-fluoro-2-(4H-1,2,4-triazol-4-yl)benzophenone;
2'-chloro-3-(trifluoromethyl)-2-(4H-1,2,4-triazol-4-yl)benzophenone;
3-(trifluoromethyl)-2-(4H-1,2,4-triazol-4-yl)benzophenone;
4-chloro-2-(4H-1,2,4-triazol-4-yl)benzophenone;
6-nitro-2-(4H-1,2,4-triazol-4-yl)benzophenone;

3'-chloro-6-trifluoromethyl-2-(4H-1,2,4-triazol-4-yl)benzophenone;
4'-fluoro-2-(4H-1,2,4-triazol-4-yl)benzophenone;
2'-fluoro-5-trifluoromethyl-2-(4H-1,2,4-triazol-4-yl)benzophenone;
5-bromo-2-(4H-1,2,4-triazol-4-yl)benzophenone;
5-bromo-2'-fluoro-2-(4H-1,2,4-triazol-4-yl)benzophenone;
6-bromo-2-(4H-1,2,4-triazol-4-yl)benzophenone;
2-(4H-1,2,4-triazol-4-yl)benzophenone; and the like.

Example 2:
5-Chloro-2-[3,5-bis(hydroxymethyl)-4H-1,2,4-triazol-4-yl]benzophenone A stirred mixture of 5-chloro-2-(4H-1,2,4-triazol-4-yl)benzophenone (2.84 g, 0.01 mole), paraformaldehyde (3.0 g) and xylene (100 ml) is warmed, under nitrogen, in an oil bath at 118°–124° C for 1 hour 20 minutes and concentrated in vacuo. The residue is dissolved in methylene chloride, filtered and the filtrate concentrated and crystallized from ethanol-ethyl acetate to give: 0.916 g of an ethyl acetate solvate of 5-chloro-2-[3,5-bis(hydroxymethyl)-4H-1,2,4-triazol-4-yl]benzophenone of melting point 199°–200.5°C., and additionally 1.642 g of melting point 200°–200.5° C and 0.452 g of melting point 200.5°–201.5°C. The analytical sample had melting point of 201.5°–202.5°C.

Anal. calcd for $C_{17}H_{14}ClN_3O_3$: C, 59.40; H, 4.10; Cl, 10.31; N, 12.22.

Found: C, 59.49; H, 4.47; Cl, 9.76; N, 11.59; Ethyl acetate, 6.07. When corrected for 6.07% ethyl acetate, the analysis is: C, 59.83; H, 4.18; Cl, 10.39; N, 12.34.

Example 3:
2',5-Dichloro-2-[3,5-bis(hydroxymethyl)-4H-1,2,4-triazol-4-yl]benzophenone In the manner given in Example 2, 2',5-dichloro-2-(4H-1,2,4-triazol-4-yl)benzophenone in xylene is heated with paraformaldehyde to 118°–124°C to give 2',5-dichloro-2-[3,5-bis(hydroxymethyl)-4H-1,2,4-triazol-4-yl]benzophenone.

Example 4:
2'-chloro-5-fluoro-2-[3,5-bis(hydroxymethyl)-4H-1,2,4-triazol-4-yl]benzophenone In the manner given in Example 2, 2'-chloro-5-fluoro-2-(4H-1,2,4-triazol-4-yl)benzophenone in xylene is heated with paraformaldehyde to 118°–124°C to give 2'-chloro-5-fluoro-2-[3,5-bis(hydroxymethyl)-4H-1,2,4-triazol-4-yl]benzophenone.

Example 5:
2'-Chloro-5-trifluoromethyl-2-[3,5-bis(hydroxymethyl)-4H-1,2,4-triazol-4-yl]benzophenone In the manner given in Example 2, 2'-Chloro-5-trifluoromethyl-2-(4H-1,2,4-triazol-4-yl)benzophenone in xylene is heated with paraformaldehyde to 118°–124°C to give 2'-chloro-5-trifluoromethyl-2-[3,5-bis(hydroxymethyl)-4H-1,2,4-triazol-4-yl]benzophenone.

Example 6:
5-Chloro-2',6'-difluoro-2-[3,5-bis(hydroxymethyl)-4H-1,2,4-triazol-4-yl]benzophenone In the manner given in Example 2, 5-chloro-2',6'-difluoro-2-(4H-1,2,4-triazol-4-yl)benzophenone in xylene is heated with paraformaldehyde to 118°–124° C to give 5-chloro-2',6'-difluoro-2-[3,5-bis(hydroxymethyl)-4H-1,2,4-triazol-4-yl]benzophenone.

Example 7:
5-Nitro-2-[3,5-bis(hydroxymethyl)-4H-1,2,4-triazol-4-yl]benzophenone In the manner given in Example 2, 5-nitro-2l-(4H-1,2,4-triazol-4-yl)benzophenone in xylene is heated with paraformaldehyde to 118°–124°C to give 5-nitro-2-[3,5-bis-(hydroxymethyl)-4H-1,2,4-triazol-4-yl]benzophenone.

Example 8:
2'-Chloro-5-nitro-2-[3,5-bis(hydroxymethyl)-4H-1,2,4-triazol-4-yl]benzophenone In the manner given in Example 2, 2'-chloro-5-nitro-2-(4H-1,2,4-triazol-4-yl)benzophenone in xylene is heated with paraformaldehyde to 118°–124°C to give 2'-chloro-5-nitro-2-]3,5-bis(hydroxymethyl)-4H-1,2,4-triazol-4-yl]benzophenone.

Example 9:
5-Bromo-2-[3,5-bis(hydroxymethyl)-4H-1,2,4-triazol-4-yl]benzophenone In the manner given in Example 2, 5-bromo-2-(4H-1,2,4-triazol-4-yl)benzophenone in xylene is heated with paraformaldehyde to 118°–124°C to give 5-bromo-2-[3,5-bis(hydroxymethyl)-4H-1,2,4-triazol-4-yl]benzophenone.

Example 10:
5-Bromo-2'-fluoro-2-[3,5-bis(hydroxymethyl)-4H-1,2,4-triazol-4-yl]benzophenone In the manner given in Example 2, 5-bromo-2'-fluoro-2-(4H-1,2,4-triazol-4-yl)benzophenone in xylene is heated with paraformaldehyde to 118°–124°C to give 5-bromo-2'-fluoro-2-[3,5-bis(hydroxymethyl)-4H-1,2,4-triazol-4-yl]benzophenone.

Example 11:
2-[3,5-bis(hydroxymethyl)-4H-1,2,4-triazol-4-yl]benzophenone

In the manner given in Example 2, 2-(4H-1,2,4-triazol-4-yl)benzophenone in xylene is heated with paraformaldehyde to 118°–124°C to give 2-[3,5-bis(hydroxymethyl)-4H-1,2,4-triazol-4-yl]benzophenone.

Example 12:
5-Chloro-2-[3,5-bis(phthalimidomethyl)-4H-1,2,4-triazol-4-yl]benzophenone A stirred mixture of 5-chloro-2-[3,5-bis(hydroxymethyl)-4H-1,2,4-triazol-4-yl]benzophenone (2.06g, 0.006 mole), phthalimide (1.94 g, 0.0132 mole) and triphenylphosphine (3.46 g, 0.0132 mole) in dry tetrahydrofuran (60 ml), under nitrogen, is treated during 10 minutes with diethyl azodicarboxylate (2.30 g, 0.0132 mole). (A slight exothermic reaction occurs during the addition and is moderated with an ice-water bath.) The suspended solid dissolves; the solution is allowed to stand at ambient temperature for 18 hours. It is concentrated in vacuo and the residue is mixed with water and extracted with chloroform. The extract is washed with brine, dried over anhydrous sodium sulfate and concentrated. The residue is chromatographed on silica gel (200 g) with 2% methanol-98% chloroform. The resulting product is crystallized from methanolmethylene chloride to give: 0.935 g of 5-chloro-2-[3,5-bis(phthalimidomethyl)-4H-1,2,4-triazol-4-yl]benzophenone of melting point 251.5°–253.5°C; and 0.580 g of melting point 250.5°–252°C; 0.872 g of melting point 251°–253° and 0.201 g of melting point 250°–251° (71.6% yield). The analytical sample has melting point 250.5°–252.5° C.

Anal. Calcd for $C_{33}H_{20}ClN_5O_5$: C, 65.84; H, 3.35; Cl, 5.89; N, 11.63. Found: C, 66.02; H, 3.34; Cl, 5.95; N, 11.62.

Example 13:
2',5-dichloro-2-[3,5-bis(phthalimidomethyl)-4H-1,2,4-triazol-4-yl]benzophenone In the manner given in Example 12, 2',5-dichloro-2-[3,5-bis(hydroxymethyl)-4-H-1,2,4-triazol-4-yl]benzophenone, phthalimide, and triphenylphosphine in tetrahydrofuran is reacted with diethyl azodicarboxylate to give 2',5-dichloro-2-[3,5-bis(phthalimidomethyl)-4-H-1,2,4-triazol-4-yl]benzophenone.

Example 14:
5-Nitro-2-[3,5-bis(phthalimidomethyl)-4H-1,2,4-triazol-4-yl]benzophenone In the manner given in Example 12, 5-nitro-2-[3,5-bis(hydroxymethyl)-4-H-1,2,4-triazol-4-yl]benzophenone, phthalimide, and triphenylphosphine in tetrahydrofuran is reacted with diethyl azodicarboxylate to give 5-nitro-2-[3,5-bis(phthalimidomethyl)-4H-1,2,4-triazol-4-yl]benzophenone.

Example 15:
2'-Chloro-5-fluoro-2-[3,5-bis(phthalimidomethyl)-4H-1,2,4-triazol-4-yl]benzophenone In the manner given in Example 12, 2'-chloro-5-fluoro-2-[3,5-bis(hydroxymethyl)-4H-1,2,4-triazol-4-yl]benzophenone, phthalimide, and triphenylphosphine in tetrahydrofuran is reacted with diethyl azodicarboxylate to give 2'-chloro-5-fluoro-2-[3,5-bis(phthalimidomethyl)-4H-1,2,4-triazol-4-yl]-benzophenone.

Example 16:
2'-Chloro-5-trifluoromethyl-2-[3,5-bis(phthalimidomethyl)-4H-1,2,4-triazol-4-yl]benzophenone In the manner given in Example 12, 2'-chloro-5-trifluoromethyl-2-[3,5-bis(hydroxymethyl)-4H-1,2,4-triazol-4-yl]benzophenone, phthalimide, and triphenylphosphine in tetrahydrofuran is reacted with diethyl azodicarboxylate to give 2'-chloro-5-trifluoromethyl-2-[3,5-bis(phthalimidomethyl)-4H-1,2,4-triazol-4-yl]benzophenone.

Example 17:
2',6'-Difluoro-5-chloro-2-[3,5-bis(phthalimidomethyl)-4H-1,2,4-triazol-4-yl]benzophenone In the manner given in Example 12, 2',6'-difluoro-5-chloro-2-[3,5-bis(hydroxymethyl)-4H-1,2,4-triazol-4-yl]benzophenone, phthalimide, and triphenylphosphine in tetrahydrofuran is reacted with diethyl azodicarboxylate to give 2',6'-difluoro-5-chloro-2-[3,5-bis(phthalimidomethyl)-4H-1,2,4-triazol-4-yl]benzophenone.

Example 18:
2'-Chloro-5-nitro-2-[3,5-bis(phthalimidomethyl)-4H-1,2,4-triazol-4-yl]benzophenone.

In the manner given in Example 12, 2'-chloro-5-nitro-2-[3,5-bis(hydroxymethyl)-4H-1,2,4-triazol-4-yl]benzophenone, phthalimide, and triphenylphosphine in tetrahydrofuran is reacted with diethyl azodicarboxylate to give 2'-chloro-5-nitro-2-[3,5-bis(phthalimidomethyl)-4H-1,2,4-triazol-4-yl]benzophenone.

Example 19:
5-Bromo-2-[3,5-bis(phthalimidomethyl)-4H-1,2,4-triazol-4-yl]benzophenone In the manner given in Example 12, 5-bromo-2-[3,5-bis-(hydroxymethyl-4H-1,2,4-triazol-4-yl]benzophenone, phthalimide, and triphenylphosphine in tetrahydrofuran is reacted with diethyl azodicarboxylate to give 5-bromo-2-[3,5-bis(phthalimidomethyl)-4H-1,2,4-triazol-4-yl]benzophenone.

Example 20:
5-Bromo-2'-fluoro-2-[3,5-bis(phthalimidomethyl)-4H-1,2,4-triazol-4-yl]benzophenone In the manner given in Example 12, 5-bromo-2-[3,5-bis-(hydroxymethyl)-4H-1,2,4-triazol-4-yl]benzophenone, phthalimide and triphenylphosphine in tetrahydrofuran is reacted with diethyl azodicarboxylate to give 5-bromo-2'-fluoro-2-[3,5-bis(phthalimidomethyl)-4H-1,2,4-triazol-4-yl]benzophenone.

Example 21:
2-[3,5-bis(phthalimidomethyl)-4H-1,2,4-triazol-4-yl]benzophenone In the manner given in Example 12, 2-[3,5-bis(hydroxymethyl)-4H-1,2,4-triazol-4-yl]benzophenone, phthalimide and triphenylphosphine in tetrahydrofuran is reacted with diethyl azodicarboxylate to give 2-[3,5-bis(phthalimidomethyl)4H-1,2,4-triazol-4-yl]benzophenone.

Example 22:
8-Chloro-1-(aminomethyl)-6-phenyl-4H-s-triazolo[4,3-a][1,4]benzodiazepine.

A stirred mixture of 5-chloro-2-[3,5-bis(phthalimidomethyl)-4H-1,2,4-triazol-4-yl]benzophenone (1.81 g, 0.003 mole) and absolute ethanol (30 ml) is treated with hydrazine hydrate (0.437 ml, 0.009 mole) and kept in an oil bath at 72°–76°C for two hours and 20 minutes. During this period the phthalimide dissolves and a second solid forms. The mixture is cooled in an ice bath and filtered. The solid is washed with ethanol and methylene chloride. The filtrate is concentrated in vacuo. This residue is mixed with cold water and extracted with chloroform. The extract is washed (brine), dried over anhydrous sodium sulfate and concentrated in vacuo to give 8-chloro-1-(aminomethyl)-6-phenyl-4H-s-triazolo[4,3-a][1,4]benzodiazepine as a crude oil.

Example 23:
8-Chloro-1-[(dimethylamino)methyl]-6-phenyl-4H-s-triazolo[4,3-a][1,4]benzodiazepine A solution of the crude 8-chloro-1-[(aminomethyl)]-6-phenyl-4H-s-triazolo[4,3-a][1,4]benzodiazepine in acetonitrile is treated successively with 37% formalin (1.5 ml) and sodium cyanoborohydride (0.375 g). During the next 1 hour 20 minutes, 2 ml. of a 10% (v/v) solution of acetic acid in acetonitrile is added periodically, dropwise in such a manner that the temperature of the mixture remains between 25°–30° without external cooling. When the reaction is complete, the pH of the solution is about 6.8 and no further rise in temperature is noted after the addition of acid. The mixture is stirred for an additional 25 minutes and concentrated in vacuo. The residue is dissolved in methanol and concentrated. This residue is dissolved in methanol (30 ml), treated with 25% aqueous ethylenediamine (15 ml) and refluxed for 45 minutes. The mixture is cooled, diluted with water, saturated with sodium chloride and extracted with chloroform. The extract is washed (brine), dried over anhydrous sodium sulfate and concentrated. The residue is chromatographed on silica gel (100 g) with 2% methanol-98% chloroform. The resulting product is crystallized from ethyl acetate-Skellysolve B hexanes to give 8-chloro-1-[(dimethylamino)methyl]-6-phenyl-4H-s-triazolo[4,3-a][1,4]benzodiazepine in 2 crops: 330 mg. of melting point 170°–172.5°C; 67 mg. of melting point 168°–171°C (total yield 37.6%).

Example 24:
8-Chloro-1-(aminomethyl)-6-(o-chlorophenyl)-4H-s-triazolo[4,3-a][1,4]benzodiazepine In the manner given in Example 22,
2',5-dichloro-2-[3,5-bis(phthalimidomethyl)-4H-1,2,4-triazol-4-yl]benzophenone in ethanol is heated with hydrazine hydrate to give
8-chloro-1-(aminomethyl)-6-(o-chlorophenyl)-4H-s-triazol[4,3-a][1,4]benzodiazepine.

Example 25:
8-Chloro-1-[(dimethylamino)methyl]-6-(o-chlorophenyl)-4H-s-triazolo[4,3-a][1,4]benzodiazepine In the manner given in Example 23 a solution of 8-chloro-1-(aminomethyl)-6-(o-chlorophenyl)-4H-s-triazolo[4,3-a][1,4]benzodiazepine in acetonitrile is treated with formalin, sodium cyanoborohydride and acetic acid to give 8-chloro-1-[(dimethylamino)methyl]-6-(o-chlorophenyl)-4H-s-triazolo[4,3-a][1,4]benzodiazepine.

Example 26:
8-Nitro-1-(aminomethyl)-6-phenyl-4H-s-triazolo[4,3-a][1,4]benzodiazepine In the manner given in Example 22, 5-nitro-2-[3,5-bis-(phthalimidomethyl)-4H-1,2,4-triazol-4-yl]benzophenone in ethanol is heated with hydrazine hydrate to give 8-nitro-1-(aminomethyl)-6-phenyl-4H-s-triazolo[4,3-a][1,4]benzodiazepine.

Example 27:
8-Nitro-1-[(dimethylamino)methyl]-6-phenyl-4H-s-triazolo[4,3-a][1,4]benzodiazepine In the manner given in Example 23, a solution of 8-nitro-1-(aminomethyl)-6-phenyl-4H-s-triazolo[4,3-a][1,4]benzodiazepine in acetonitrile is treated with formalin, sodium cyanoborohydride and acetic acid to give 8-nitro-1-[(dimethylamino)methyl]-6-phenyl-4H-s-triazolo[4,3-a][1,4]benzodiazepine.

Example 28:
8-Nitro-1-(aminomethyl)-6-(o-chlorophenyl)4H-s-triazolo[4,3-a][1,4]benzodiazepine In the manner given in Example 22, 5-nitro-2'-chloro-2-[3,5-bis(phthalimidomethyl)-4H-1,2,4-triazol-4-yl]benzophenone in ethanol is heated with hydrazine hydrate to give 8-nitro-1-(aminomethyl)-6-(o-chlorophenyl)-4H-s-triazolo[4,3-a][1,4]enzodiazepine.

Example 29:
8-nitro-1-[(dimethylamino)methyl]-6-(o-chlorophenyl)-4H-s-triazolo[4,3-a][1,4]benzodiazepine

In the manner given in Example 23 a solution of 8-nitro-1-(aminomethyl)-6-(o-chlorophenyl)-4H-s-triazolo[4,3-a][1,4]benzodiazepine in acetonitrile is treated with formalin, sodium cyanoborohydride and propionic acid to give 8-nitro-1-[(dimethylamino)methyl]-6-(o-chlorophenyl)4H-s-triazolo[4,3-a][1,4]benzodiazepine.

Example 30:
8-Chloro-1-(aminomethyl)-6-(2,6-difluorophenyl-4H-s-triazolo[4,3-a][1,4]benzodiazepine In the manner given in Example 22, 5-chloro-2',6'-difluoro-2-[3,5-bis(phthalimidomethyl)-4H-1,2,4-triazol-4-yl]benzophenone in ethanol is heated with hydrazine hydrate to give 8-chloro-1-(aminomethyl)-6-(2,6-difluorophenyl)-4H-s-triazolo[4,3-a][1,4]benzodiazepine.

Example 31:
8-Chloro-1-[(dimethylamino)methyl]-6-(2,6-difluorophenyl)-4H-s-triazolo[4,3-a][1,4]benzodiazepine In the manner given in Example 23, a solution of 8-chloro-1-(aminomethyl)-6-(2,6-difluorophenyl)-4H-s-triazolo[4,3-a][1,4]benzodiazepine in acetonitrile is treated with formalin, sodium cyanoborohydride and acetic acid to give 8-chloro-1-[(dimethylamino)methyl]-6-(2,6-difluorophenyl)-4H-s-triazolo[4,3-a][1,4]benzodiazepine.

Example 32:
8-Fluoro-1-(aminomethyl)-6-(o-chlorophenyl)-4H-s-triazolo[4,3-a][1,4]benzodiazepine In the manner given in Example 22, 5-fluoro-2'-chloro-2-[3,5-bis(phthalimidomethyl)-4H-1,2,4-triazol-4-yl]benzophenone in ethanol is heated with hydrazine hydrate to give 8-fluoro-1-(aminomethyl)-6-(o-chlorophenyl)-4H-s-triazolo[4,3-a][1,4]benzodiazepine.

Example 33:
8-Fluoro-1-[(dimethylamino)methyl]-6-(o-chlorophenyl)-4H-s-triazolo[4,3-a][1,4]benzodiazepine In the manner given in Example 23, a solution of 8-fluoro-1-(aminomethyl)-6-(o-chlorophenyl)-4H-s-triazolo[4,3-a][1,4]benzodiazepine in acetonitrile is treated with formalin, sodium cyanoborohydride and acetic acid to give 8-fluoro-1-[(dimethylamino)methyl]-6-(o-chlorophenyl)4H-s-triazolo[4,3-a][1,4]benzodiazepine.

Example 34:
8-Trifluoromethyl-1-(aminomethyl)-6-(o-chlorophenyl)-4H-s-triazolo[4,3-a][1,4]benzodiazepine In the manner given in Example 22, 5-trifluoromethyl-2'-chloro-2-[3,5-bis(phthalimidomethyl)-4H-1,2,4-triazol4-yl]benzophenone in ethanol is heated with hydrazine hydrate to give 8-trifluoromethyl-1-(aminomethyl)-6-(o-chlorophenyl)-4H-s-triazolo[4,3-a][1,4]benzodiazepine.

Example 35:
8-Trifluoromethyl-1-[(dimethylamino)methyl]-6-(o-chlorophenyl)-4H-s-triazolo[4,3-a][1,4]benzodiazepine In the manner given in Example 23, a solution of 8-trifluoromethyl-1-(aminomethyl)-6-(o-chlorophenyl)-4H-s-triazolo[4,3-a][1,4]benzodiazepine in acetonitrile is treated with formalin, sodium cyanoborohydride and acetic acid to give 8-trifluoromethyl-1-[(dimethylamino)methyl]-6-(o-chlorophenyl)-4H-s-triazolo[4,3-a][1,4]benzodiazepine.

Example 36:
8-Bromo-1-(aminomethyl)-6-phenyl-4H-s-triazolo[4,3-a][1,4]benzodiazepine In the manner given in Example 22, 5-bromo-2-[3,5-bis(phthalimidomethyl)-4H-1,2,4-triazol-4-yl]benzophenone in ethanol is heated with hydrazine hydrate to give 8-bromo-1-(aminomethyl)-6-phenyl-4H-s-triazolo[4,3-a][1,4]benzodiazepine.

Example 37:
8-Bromo-1-[(dimethylamino)methyl]-6-phenyl-4-H-s-triazolo[4,3-a][1,4]benzodiazepine In the manner given in Example 23, a solution of 8-bromo-1-(aminomethyl)-6-phenyl-4H-s-triazolo[4,3-a][1,4]benzodiazepine in acetonitrile is treated with formalin, sodium cyanoborohydride and acetic acid to give 8-bromo-1-[(dimethylamino)methyl]-6-phenyl-4H-s-triazolo[4,3-a][1,4]benzodiazepine.

Example 38:
8-Bromo-1-(aminomethyl)-6-(o-flurophenyl)-4H-s-triazolo[4,3-a][1,4]benzodiazepine In the manner given in Example 22, 5-bromo-2'-fluoro-2-[3,5-bis(phthalimidomethyl)-4H-1,2,4-triazol-4-yl]benzophenone in ethanol is heated with hydrazine hydrate to give 8-bromo-1-(aminomethyl)-6-(o-fluorophenyl)-4H-s-triazolo[4,3-a][1,4]benzodiazepine.

Example 39:
8-Bromo-1-[(dimethylamino)methyl]-6-(o-fluorophenyl)-4H-s-triazolo[4,3-a][1,4]benzodiazepine In the manner given in Example 23, a solution of 8-bromo-1-(aminomethyl)-6-(o-fluorophenyl)-4H-s-triazolo[4,3-a][1,4]benzodiazepine in acetonitrile is treated with formalin, sodium cyanoborohydride and acetic acid to give 8-bromo-1-[(dimethylamino)methyl]-6-(o-fluorophenyl)-4H-s-triazolo[4,3-a][1,4]benzodiazepine.

Example 40:
1-(aminomethyl)-6-phenyl-4H-s-triazolo[4,3-a][1,4]benzodiazepine In the manner given in Example 22, 2-[3,5-bis(phthalimidomethyl)-4H-1,2,4-triazol-4-yl]benzophenone in ethanol is heated with hydrazine hydrate to give 1-(aminomethyl)6-phenyl-4H-s-triazolo[4,3-a][1,4]benzodiazepine.

Example 41:
1-[(dimethylamino)methyl]-6-phenyl-4H-s-triazolo[4,3-a][1,4]benzodiazepine In the manner given in Example 23, a solution of 1-(aminomethyl)-6-phenyl-4H-s-triazolo[4,3-a][1,4]benzodiazepine in acetonitrile is treated with formalin, sodium cyanoborohydride and acetic acid to give 1-[(dimethylamino)methyl]6-phenyl-4H-s-triazolo[4,3-a][1,4]benzodiazepine.

Example 42:
8-Chloro-1-[(diethylamino)methyl]-6-phenyl-4H-s-triazolo[4,3-a][1,4]benzodiazepine In the manner given in Example 23, a solution of 8-chloro-1-(aminomethyl)-6-phenyl-4H-s-triazolo[4,3-a][1,4]benzodiazepine in acetonitrile is treated with acetaldehyde, sodium cyanoborohidride and acetic acid to give 8-chloro-1-[(diethylamino)methyl]-6-phenyl-4H-s-triazolo[4,3-a][1,4]benzodiazepine.

Example 43:
8-chloro-1-[(dipropylamino)methyl]-6-(o-chlorophenyl)-4H-s-triazolo[4,3-a][1,4]benzodiazepine In the manner given in Example 23, a solution of 8-chloro-1-(aminomethyl)-6-(o-chlorophenyl)-4H-s-triazolo[4,3-a][1,4]benzodiazepine in acetonitrile is treated with propionaldehyde, sodium cyanoborohydride and acetic acid to give 8-chloro-1-[(dipropylamino)methyl]-6-(o-chlrophenyl)4-H-s-triazolo[4,3-a][1,4]benzodiazepine.

Example 44:
8-Chloro-1-[(diethylamino)methyl]-6-(o-chlorophenyl)-4H-s-triazolo[4,3-a][1,4]benzodiazepine In the manner given in Example 23, a solution of 8-chloro-1-(aminomethyl)-6-(o-chlorophenyl)-4H-s-traizolo[4,3-a][1,4]benzodiazepine in acetonitrile is treated with acetaldehyde, sodium cyanoborohydride and acetic acid to give 8-chloro-1-[(diethylamino)methyl]-6-(o-chlorophenyl)4H-s-triazolo[4,3-a][1,4]benzodiazepine.

Example 45:
8-Chloro-1-[(dipropylamino)methyl]-6-(o-fluorophenyl)-4H-s-triazolo[4,3-a][1,4]benzodiazepine In the manner given in Example 23, a solution of 8-chloro-1-(aminomethyl)-6-(o-fluorophenyl)-4H-s-triazolo[4,3-a][1,4]benzodiazepine in acetonitrile is treated with propionaldehyde, sodium cyanoborohydride and acetic acid to give 8-chloro-1-[(dipropylamino)methyl]-6-(o-fluorophenyl)-4H-s-traizolo[4,3-a][1,4]benzodiazepine.

Example 46:
8-Chloro-1-[(dimethylamino)methyl]-6-(o-fluorophenyl)-4H-s-triazolo[4,3-a][1,4]benzodiazepine In the manner given in Example 23, a solution of 8-chloro-1-(aminomethyl)-6-(o-fluorophenyl)-4H-s- triazolo[4,3-a][1,4]benzodiazepine in acetonitrile is treated with formalin, sodium cyanoborohydride and acetic acid to give 8-chloro-1-[(dimetnylamino)methyl]-6-(o-fluorophenyl)-4H-s-triazolo[4,3-a][1,4]benzodiazepine.

In the manner illustrated by the preceeding examples other 1-(substituted or unsubstituted aminomethyl)-6-phenyl-4H-s-triazolo[4,3-a][1,4]benzodiazepines can be prepared. Representative compounds thus obtained include:

8-nitro-1-[(diethylamino)methyl)]-6-(o-fluorophenyl)-4H-s-triazolo[4,3-a][1,4]benzodiazepine;
8-chloro-1-[(diethylamino)methyl)]-6-(2,6-difluorophenyl)-4H-s-triazolo[4,3-a][1,4]benzodiazepine;
8-fluoro-1-(aminomethyl)-6-phenyl-4H-s-triazolo[4,3-a]-[1,4]benzodiazepine;
9-chloro-1-[(dimethylamino)methyl]-6-phenyl-4H-s-triazolo[4,3-a][1,4]benzodiazepine;
9-chloro-1-[(diethylamino)methyl]-6-(o-chlorophenyl)-4H-s-triazolo[4,3-a][1,4]benzodiazepine;
7-trifluoromethyl-1-(aminomethyl)-6-(m-chlorophenyl)-4H-s-triazolo[4,3-a][1,4]benzodiazepine;
9-fluoro-1-[(dimethylamino)methyl]-6-phenyl-4H-s-triazolo[4,3-a][1,4]benzodiazepine;
7-trifluoromethyl-1-[(dimethylamino)methyl]-6-(m-chlorophenyl)-4H-s-triazolo[4,3-a][1,4]benzodiazepine;
10-trifluoromethyl-1-(aminomethyl)-6-phenyl-4H-s-triazolo[4,3-a][1,4]benzodiazepine;
10-chloro-1-[(diethylamino)methyl]-6-(o-chlorophenyl)-4H-s-triazolo[4,3-a][1,4]benzodiazepine;
10-chloro-1-(aminomethyl)-6-(o-chlorophenyl)-4H-s-triazolo[4,3-a][1,4]benzodiazepine;
8-bromo-1-[(diethylamino)methyl]-6-phenyl-4H-s-trizolo[4,3-a][1,4]benzodiazepine;
8-bromo-1-[(dipropylamino)methyl]-6-phenyl-4H-s-triazolo[4,3-a][1,4]benzodiazepine;
8-bromo-1-[(diethylamino)methyl]-6-(o-fluorophenyl)-4H-s-triazolo[4,3a][1,4]benzodiazepine;
8-bromo-1-[(dipropylamino)methyl]-6-(o-fluorophenyl)-4H-s-triazolo[4,3-a][1,4]benzodiazepine;
1-[(diethylamino)methyl]-6-phenyl-4H-s-triazolo[4,3-a][1,4]benzodiazepine;
1-[(dipropylamino)methyl]-6-phenyl-4H-s-triazolo[4,3-a][1,4]benzodiazepine;
and the like.

We claim:
1. A process for the production of a compound of the formula V:

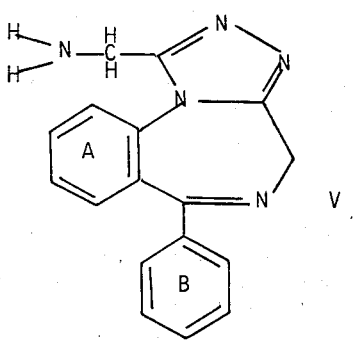

wherein the rings A and B are unsubstituted or substituted by chloro, fluoro, bromo, nitro or trifluoromethyl, which comprises:
1. reacting a compound of formula I

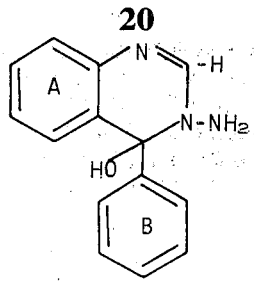

wherein a and B are defined as above, with an equimolar mixture of formic acid and acetic anhydride at 0° to 25°C and then warming the mixture at 90°–118° to obtain the corresponding compound of formula II:

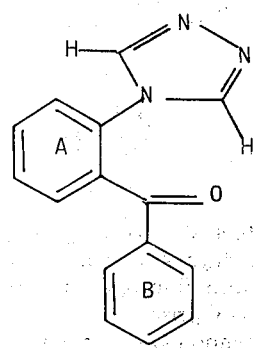

wherein rings A and B are defined as above;
2. heating in an inert organic solvent a compound of formula II with paraformaldehyde to between 118° and 150°C., to obtain the corresponding compound III:

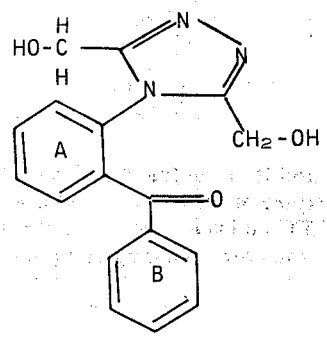

wherein rings A and B are defined as above;
3. treating compound III, dissolved in an inert organic solvent, with phthalimide, triphenylphosphine and diethyl azodicarboxylate at a temperature between 0° and 35°C., to obtain the corresponding compound IV:

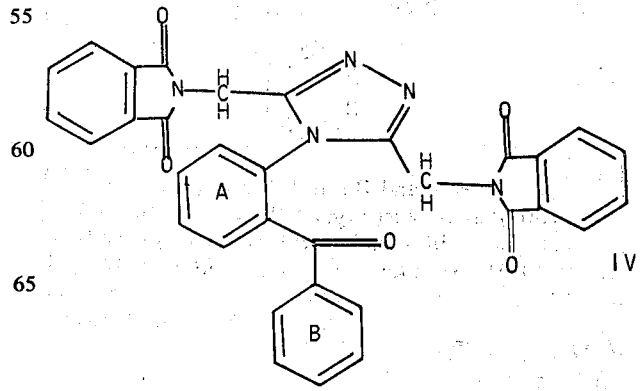

wherein rings A and B are defined as above;
4. treating the compound of formula IV with hydrazine hydrate at 60° to 100°C in an alkanol of 1 to 3 carbon atoms, inclusive, to obtain the compound of formula V as defined above.

2. A process for the production of a compound of the formula VIA:

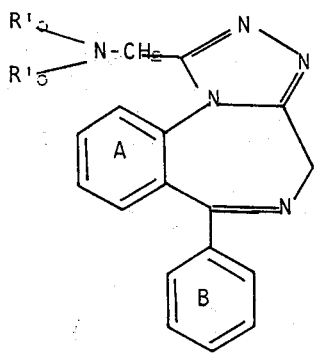

wherein $R'_o$ is alkyl of 1 to 3 carbon atoms inclusive and wherein the rings A and B are unsubstituted or substituted by chloro, fluoro, bromo, nitro, and trifluoromethyl, which comprises:

1. reacting a compound of formula I:

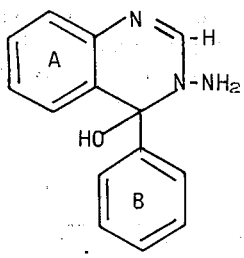

wherein A and B are defined as above, with an equimolar mixture of formic acid and acetic anhydride at 0° to 25°C and warming the mixture at 90°–118° to obtain the corresponding compound of formula II:

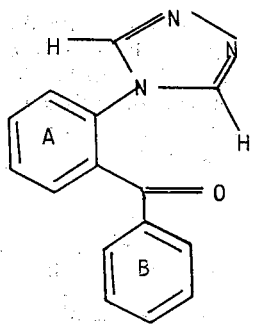

wherein rings A and B are defined as above;
2. heating in an inert organic solvent a compound of formula II with paraformaldehyde to between 118° and 150°, to obtain the corresponding compound III:

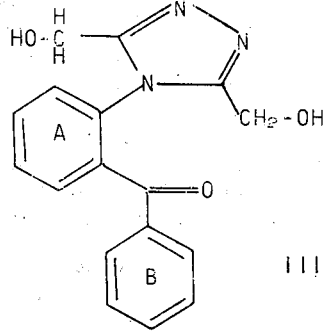

wherein rings A and B are defined as above;
3. treating compound III, dissolved in an inert organic solvent, with phthalimide, triphenylphosphine and diethyl azodicarboxylate at a temperature between 0° and 35°C., to obtain the corresponding compound IV:

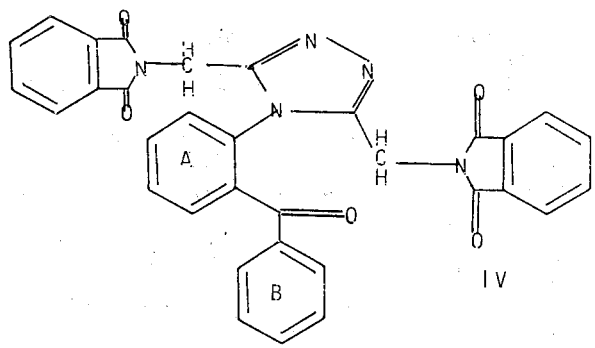

wherein rings A and B are defined as above:
4. treating the compound of formula IV with hydrazine hydrate at 60° to 100°C in an alkanol of 1 to 3 carbon atoms inclusive to obtain the corresponding compound of formula V:

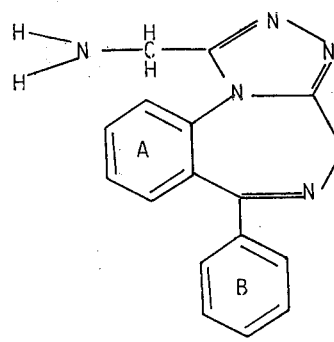

wherein rings A and B are defined as above; and
5. alkylating compound V with carboxaldeyhyde of 1 to 3 carbon atoms, inclusive, sodium cyanoborohydride and acetic acid to obtain the corresponding compound VIA as defined above.

3. The process of claim 1 wherein in step 4 the alcohol is ethanol.

4. The process of claim 2 wherein the step 4 the alkanol is ethanol and wherein in step 5 the aldehyde is formaldehyde.

5. The proccess of claim 1 wherein the starting compounds of formula I are:
- 3-amino-3,4-dihydro-4-hydroxy-4-phenylquinazoline,
- 3-amino-6-chloro-3,4-dihydro-4-hydroxy-4-phenylquinazoline or
- 3-amino-6-chloro-3,4-dihydro-4-hydroxy-4-(o-chlorophenyl)quinazoline.

6. A compound of the formula III:

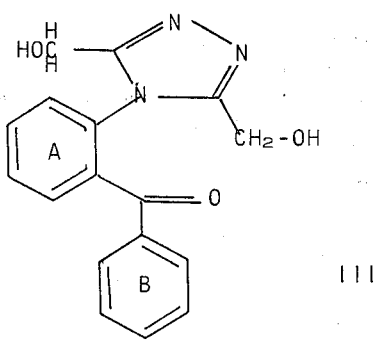

III wherein the rings A and B are unsubstituted or substituted by one or two substituents selected from the group consisting of chloro, fluoro, bromo, nitro, and trifluoromethyl.

7. A compound according to claim 6 of the formula IIIA:

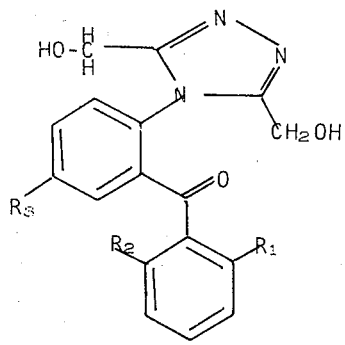

IIIA wherein $R_1$ is hydrogen, chloro or fluoro; wherein $R_2$ is hydrogen, or fluoro when $R_1$ is fluoro; and wherein $R_3$ is hydrogen, chloro, fluoro, or trifluoromethyl.

8. A compound according to claim 6 of the formula IIIB:

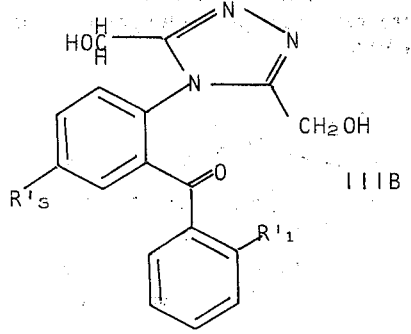

IIIB wherein $R'_1$ and $R'_3$ are hydrogen or chloro.

9. A compound according to claim 8 wherein $R'_1$ hydrogen and wherein $R'_3$ is chloro and the compound is therefore 5-chloro-2-[3,5-bis(hydroxymethyl)-4H-1,2,4-triazol-4-yl]-benzophenone.

10. A compound according to claim 8 wherein $R'_1$ is chlorine and $R'_3$ is chloro and the compound is therefore 2',5-dichloro-2-[3,5-bis(hydroxymethyl)-4H-1,2,4-triazol-4-yl]benzophenone.

11. A compound according to claim 8 wherein $R'_1$ and $R'_3$ are hydrogen and the compound is therefore 2-[3,5-bis(hydroxymethyl)-4H-1,2,4-triazol-4-yl]benzophenone.

12. A compound of the formula IV:

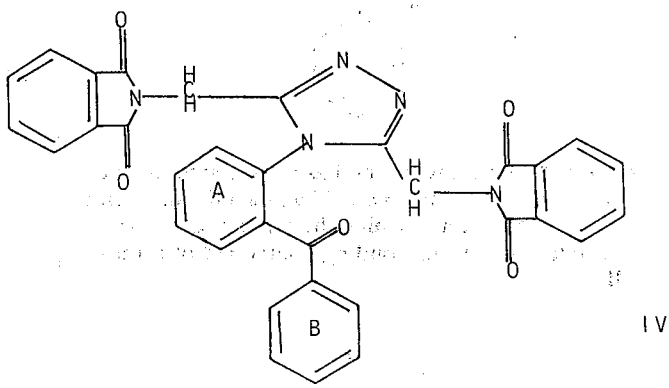

IV wherein the rings A and B are unsubstituted or substituted by one or two substituents selected from the group consisting of chloro, fluoro, bromo, nitro, and trifluoromethyl.

13. A compound according to claim 12 of the formula IVA:

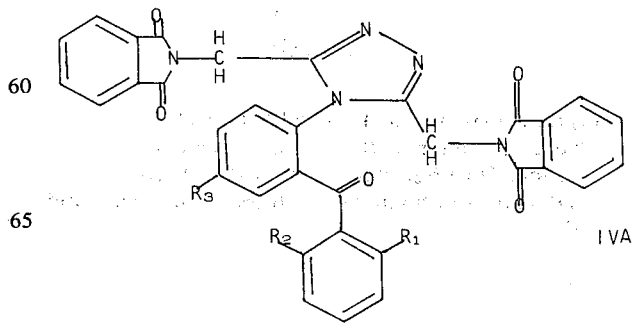

IVA wherein $R_1$ is hydrogen, chloro or fluoro; wherein $R_2$ is hydrogen, or fluoro when $R_1$ is fluoro; wherein $R_3$ is hydrogen, chloro, fluoro, or trifluoromethyl.

14. A compound according to claim 12 of the formula IVB:

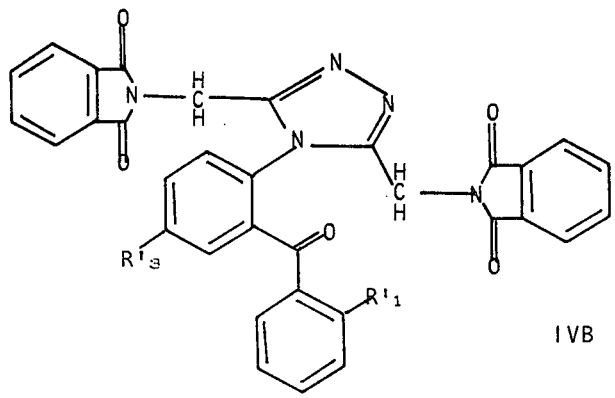

wherein $R'_1$ and $R'_3$ are hydrogen or chlorine.

15. A compound according to claim 14 wherein $R'_1$ is hydrogen and $R'_3$ is chloro and the compound is therefore 5-chloro-2-[3,5-bis(phthalimidomethyl)-4H-1,2,4-triazol-4-yl]benzophenone.

16. A compound according to claim 14 wherein $R'_1$ and $R'_3$ are chloro and the compound is therefore 2',5-dichloro-2-[3,5-bis(phthalimidomethyl)-4H-1,2,4-triazol-4-yl]benzophenone.

17. A compound according to claim 14 wherein $R'_1$ and $R'_3$ are hydrogen and the compound is therefore 2-[3,5-bis(phthalimidomethyl)-4H-1,2,4-triazol-4-yl]benzophenone.

* * * * *